US011197458B1

(12) United States Patent
Leung

(10) Patent No.: US 11,197,458 B1
(45) Date of Patent: Dec. 14, 2021

(54) BODILY WASTE COLLECTION DEVICE FOR PETS AND HUMANS

(71) Applicant: Launch Lab, Inc., Pasadena, CA (US)

(72) Inventor: Michael Leung, Pomona, CA (US)

(*) Notice: Subject to any disclaimer, the term of this patent is extended or adjusted under 35 U.S.C. 154(b) by 157 days.

(21) Appl. No.: 16/283,790

(22) Filed: Feb. 24, 2019

(51) Int. Cl.
| | | |
|---|---|---|
| *A01K 1/015* | (2006.01) | |
| *A61F 13/47* | (2006.01) | |
| *A61F 13/505* | (2006.01) | |
| *A61F 13/15* | (2006.01) | |
| *A01K 1/01* | (2006.01) | |

(52) U.S. Cl.
CPC ............ *A01K 1/0157* (2013.01); *A61F 13/47* (2013.01); *A61F 13/505* (2013.01); *A01K 1/0125* (2013.01); *A61F 2013/15008* (2013.01); *A61F 2013/16* (2013.01)

(58) Field of Classification Search
CPC .................. A61F 13/47; A61F 13/505; A61F 2013/15008; A61F 2013/16; A61F 5/48; A61F 5/485; A61F 5/4556; A61F 5/455; A01K 1/0107; A01K 1/0157; A01K 1/0125; A01K 23/005; A01K 1/00; A01K 23/00; A01K 29/00; A47G 27/0206; A47G 27/0412
USPC ........................ 604/329, 331, 354, 358–392
See application file for complete search history.

(56) References Cited

U.S. PATENT DOCUMENTS

| | | | | | |
|---|---|---|---|---|---|
| 3,284,273 | A | * | 11/1966 | Prentice | ................... A61F 5/485 428/76 |
| 3,358,647 | A | * | 12/1967 | Wilson | .................. A01K 1/0107 119/169 |
| 3,626,900 | A | * | 12/1971 | Failla | ................... A01K 1/0107 119/161 |
| 4,250,834 | A | * | 2/1981 | Cheselka | ............. A01K 1/0107 119/169 |
| 4,599,756 | A | * | 7/1986 | Koffler | ................. A47C 27/007 5/484 |
| 4,715,320 | A | * | 12/1987 | Barnhart | .............. A01K 1/0107 119/169 |
| 5,170,745 | A | * | 12/1992 | Burdette, Jr. | ........ A01K 1/0254 119/497 |
| 5,290,269 | A | * | 3/1994 | Heiman | .................. A61F 5/485 604/372 |
| 5,797,347 | A | * | 8/1998 | Ochi | .................... A01K 1/0107 119/169 |
| 6,244,216 | B1 | * | 6/2001 | Ochi | .................... A01K 1/0107 119/169 |
| 6,460,484 | B2 | * | 10/2002 | Ikegami | ............... A01K 1/0107 119/161 |
| 6,764,477 | B1 | * | 7/2004 | Chen | ................... A61F 13/4702 604/385.14 |
| 8,113,146 | B2 | * | 2/2012 | Askinasi | ............. A01K 1/0107 119/169 |
| 8,336,497 | B2 | * | 12/2012 | van Zuilekom | ..... A01K 1/0107 119/169 |

(Continued)

FOREIGN PATENT DOCUMENTS

| | | | |
|---|---|---|---|
| CN | 201078819 Y | 2/2002 | |
| EP | 0355554 A1 * | 2/1990 | ............. A61F 13/36 |
| EP | 1230845 A2 * | 8/2002 | ........... A01K 1/0353 |

*Primary Examiner* — Susan S Su

(74) *Attorney, Agent, or Firm* — David J. Wilson

(57) ABSTRACT

This invention is directed towards an absorbent bodily waste collection device for domesticated animals and humans and methods of use thereof.

13 Claims, 10 Drawing Sheets

(56) References Cited

U.S. PATENT DOCUMENTS

| | | | | |
|---|---|---|---|---|
| 2001/0025910 | A1* | 10/2001 | Olivadoti | A01K 1/0107 |
| | | | | 248/346.01 |
| 2003/0199844 | A1 | 10/2003 | Levon | |
| 2007/0283991 | A1* | 12/2007 | Sherts | A45B 23/00 |
| | | | | 135/90 |
| 2010/0154716 | A1 | 6/2010 | Smith | |
| 2010/0307422 | A1* | 12/2010 | Huck | A01K 1/0152 |
| | | | | 119/161 |
| 2011/0139082 | A1* | 6/2011 | Blagden | A01K 1/0107 |
| | | | | 119/171 |
| 2012/0226251 | A1* | 9/2012 | Rivest | A61F 13/0206 |
| | | | | 604/369 |
| 2019/0343080 | A1* | 11/2019 | Chapman | A01K 23/005 |

* cited by examiner

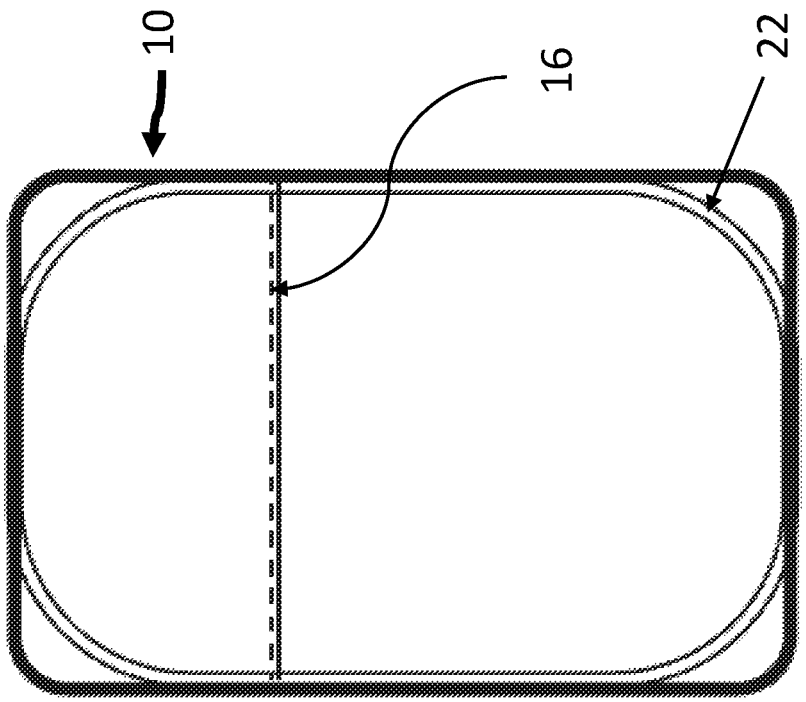
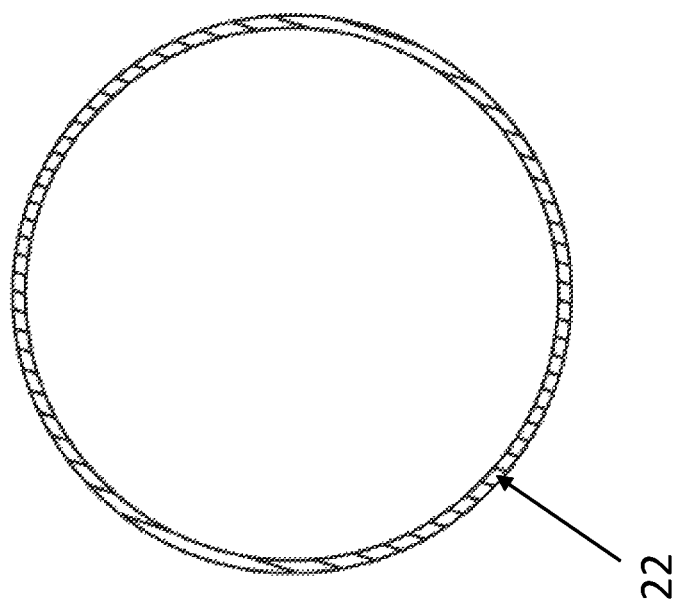
Figure 2B
Figure 2A

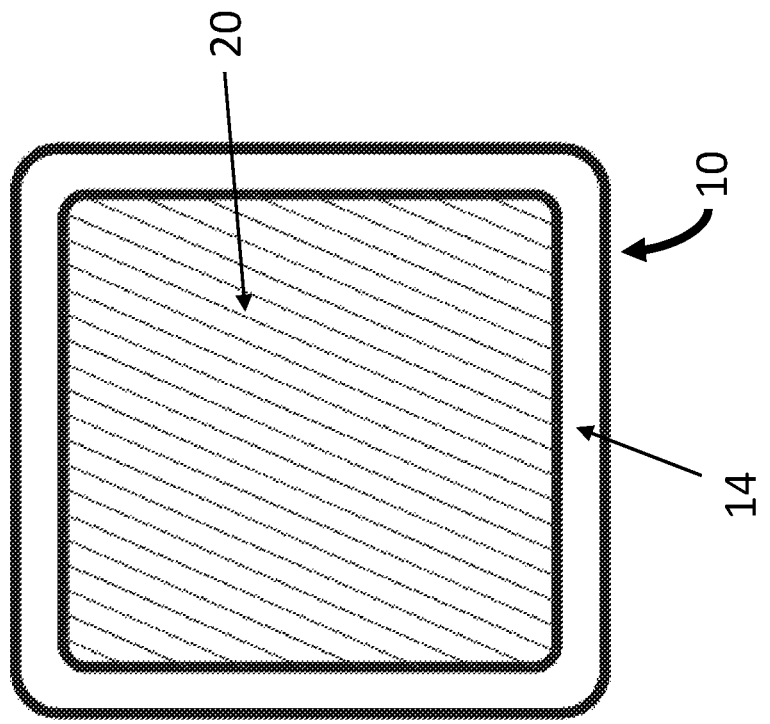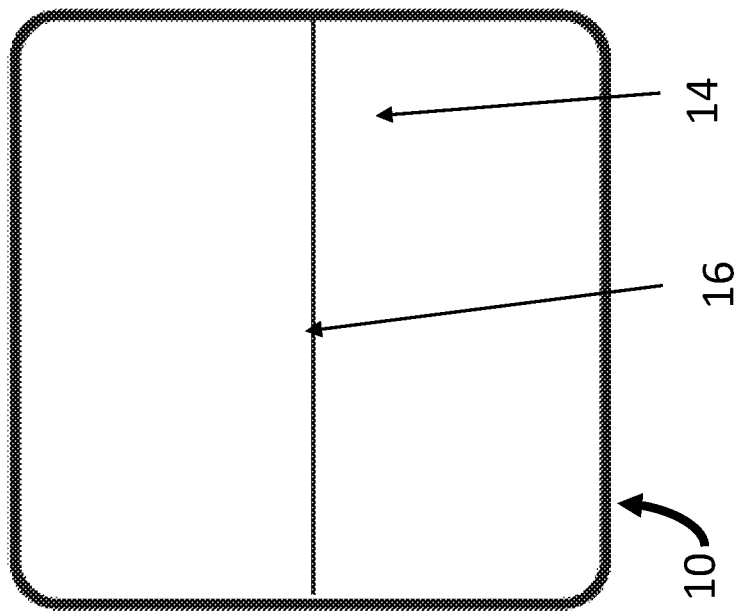

BODILY WASTE COLLECTION DEVICE FOR PETS AND HUMANS

BACKGROUND OF INVENTION

Pets and animal companions are typically trained with regard to relieving themselves. Cats are trained to use a litter box and dogs are typically trained to relieve themselves out of doors. Training for dogs can be particularly time consuming and, until the dog is fully trained, "accidents" can happen in the house or pet carrier. Further, some dogs, especially small toy breeds, are trained to use almost solely an indoor area for relieving themselves.

The pet care market has supplied many and varied devices to aid pet owners in training their animals. Among these devices are absorbent pads with a waterproof backing. To help keep the pad in place and to help maintain its shape while being used, the pads typically have adhesive strips suitable for sticking to a hard surface such as a tile floor. However, the adhesive can mar or damage the floor, can come loose if the floor is not perfectly clean prior to application or be pulled off the floor by the dog when scratching and pawing.

Some prior art devices use rubber bands to hold the absorbent pad in place. CN 200101889 teaches the use of a rubber band for holding the pad over a pet toilet. US Patent Publication No. 2010/0154716 to Smith teaches the use of a rubber band to hold the absorbent pad on to a tray inserted into a pet crate.

Further, humans can be in need of devices and methods to mitigate unwanted or uncontrolled urine releases. For example, young children may have bed wetting problems and seniors may have incontinence problems, both which can cause problems with urine being released in hard to clean areas such as beds and chairs. Diapers for larger children and for seniors are available but may not be suitable or optimal for use in all instances.

What is needed are improved alternatives to what is available to pet owners for animal training and travel with regard to absorbent pads for urinary relief. Further, what is needed are improved alternatives to what is available for people with regard to mitigating the inconvenience and damaged cause by uncontrolled or unwanted urine releases.

SUMMARY OF INVENTION

In one aspect, the invention relates to an absorbent bodily waste collection device for pets for absorbing, for example, pet urine. In particular, the urine may be from a domestic animal such as a dog. The absorbent bodily waste collection device of the present invention comprises a moisture permeable top layer, an absorbent middle layer and a moisture proof or essentially moisture proof bottom layer. The absorbent bodily waste collection device of the present invention further comprises a base layer which is at least partially attached to one or more of the bottom layer, middle layer or top layer of the absorbent pad and thereby creates a space between the base layer and the bottom layer. Thus, the absorbent bodily waste collection device of the present invention comprises an absorbent pad which comprises a top layer, a middle layer, a bottom layer and a base layer. The moisture permeable layer, absorbent middle layer and bottom layer shall collectively be referred to as the upper portion of the absorbent bodily waste collection device of the present invention.

The absorbent bodily waste collection device of the present invention further comprises a frame, the frame comprising one or more flexible frame members. The frame can be removably inserted into the space between the bottom layer and the base layer. Thus, the frame can be fit into the absorbent bodily waste collection device of the present invention. The frame comprising flexible frame member(s) is, in one embodiment, capable of conforming to the shape or sustainably conforming to the shape of the absorbent pad of the absorbent bodily waste collection device of the present invention and thereby causing the absorbent pad to remain in shape without, for example, bunching up, and without attaching the pad to a floor or other surface. That the flexible frame member can sustainably conform to the shape of the absorbent bodily waste collection device of the present invention can be especially important if the absorbent bodily waste collection device of the present invention is use in, for example, an animal crate. This element of the present invention ensures that the absorbent bodily waste collection device of the present invention can "form fit" to the shape of an area. The flexible frame member of the absorbent pad device may be made from, for example, a loop of steel (spring steel or non-spring steel) or flexible plastic. Spring steel is defined as a steel that is processed (as by cold drawing, cold rolling, or heat treating) to give it the elastic properties and yield strength useful in springs. At the very least, the steel or plastic should be flexible enough such that it can be inserted into the space located between the bottom layer and the base layer of the absorbent bodily waste collection device and substantially conform to the shape of the device. A loop of metal strapping is an example of metal suitable for use as the flexible frame member of the present invention. When used with pets, the absorbent bodily waste collection device of the present invention may be used as a stand-alone device or may be used in crates, kennels, etc.

In other aspects, the waste collection device of the present invention may utilize other types of frames to hold the waste collection device substantially flat for use. The frame may comprise, for example, rods that are inserted into channels along the edge of the waste collection device. The rods may be rigid or flexible or combine rigid and flexible portions. For example, if the rods fit together to form a square, rectangle or other shape, the portions that touch may interconnect to form a joint. These portions may be made of rigid material to give the joints greater strength. The waste collection device may be used for example, with one, two, three, four or more rods. When two rods are used with the waste collection device of the present invention, the rods may be positioned at opposite edges of the waste collection device. In this aspect, the rods may be, for example, draped over the edge of a bed or other raised surface. When three rods are used with the waste collection device of the present invention, for example, the rods may be arranged to form an "H," with the center rod separating the two edge rods, or they may be shaped to form a "U." In another aspect, one rod may be used with the rod positioned along a center line between two edges of the waste collection device of the present invention or it may be positioned anywhere along the width or length of the waste collection device. Any arrangement of rods that serves to keep the waste collection device of the present invention substantially flat for use are contemplated. In the context of the present invention, the term rod may refer to any straight or relatively straight bar, stick, wand, staff, or the like, of wood, metal or other material regardless of cross-sectional shape.

The waste collection device of the present invention need not only be used for pets. Embodiments of the present invention, appropriately sized and shaped, are suitable for human use. The waste collection device of the present invention may be used by persons with, for example, incontinence problems or may be used with small children in the event they have an "accident," i.e., urinate on furniture on in bed. In this regard, the waste collection device may be sized and shaped for use on beds, chairs, sofas and in automobiles or other vehicles.

The absorbent layer of the absorbent bodily waste collection device may be made out of any suitable absorbent material. Many such materials are known to one of ordinary skill in the art and are included for use in the present invention. Exemplary materials include, but are not limited to, cellulose, polymer fibers (e.g., polyolefin, polypropylene), cotton, absorbent clays, hydrophilic gels, etc. The amount of absorbent material used can be determined by one of ordinary skill in the art based on the device's intended use and intended user.

The moisture proof bottom layer is preferably made of a moisture proof sheet of plastic. Any suitable plastic may be used. The moisture proof bottom layer may also be made of a rubberized fabric or other rubberized material or a treated fabric such as an oil cloth or silicon treated fabric.

The moisture permeable top layer may be made from, for example, permeable plastic (made permeable by, for example, perforations or other openings made in the plastic after manufacture or by a manufacturing process that leaves openings in the plastic). Polyethylene is one example of a plastic that may be made to be permeable or manufactured to provide permeability. Moisture permeable plastics are known to those of ordinary skill in the art. Likewise, the top layer may be made from normally permeable materials such as cellulose-based materials. Further, the top layer may be perforated to provide permeability.

The base layer may be made from plastic, cloth, rubber, rubber treated fabric, etc. In an embodiment, the external surface of the base layer (the side facing, for example, the floor) may have a coating of rubber or rubberized plastic adhered to it to keep the absorbent bodily waste collection device of the present invention from sliding on the floor or other surface. The coating may cover 10%, 20%, 30%, 40%, 50%, 60%, 70%, 80%, 90% or more percent of the external surface of the base layer. The coating may be applied to substantially cover the external surface or in spots, stripes, strips, zig-zags, in a representation of a company logo or any other pattern.

The base layer may further be designed so that the flexible frame can be inserted from the side or edge of the absorbent bodily waste collection device of the present invention. In this embodiment, the base layer is attached to the remainder of the absorbent bodily waste collection device of the present invention along a portion of the edge of the upper portion of the absorbent bodily waste collection device of the present invention. The base layer may be attached along about 60%, 70%, 75%, 80% or 90% of the upper portion of the absorbent bodily waste collection device of the present invention.

The base layer may also be designed to be two overlapping or near overlapping (i.e., touching or essentially touching) portions (the first portion and the second portion). Each of the first and second portions may have a peripheral edge that conforms to the shape of about half of the periphery of the upper portion of the absorbent bodily waste collection device of the present invention. Each of the first and second portions may have a distal edge. The distal edge of the one portion may overlap, contact, contact at some points or nearly contact the distal edge of the other portion (the terms, nearly contact and contact at some points are collectively referred to herein as "essentially contact" or "essentially touch"). In this embodiment, the flexible frame is inserted into the absorbent bodily waste collection device of the present invention by separating the two distal edges to provide an opening, inserting the flexible frame into the opening and then allowing the two distal edges to return to their original positions with the flexible frame in place. Removal of the flexible frame performed in the reverse of these steps.

The layers of the absorbent pad of the present invention are fused together by, for example, heat (thermal bonding), IR welding, gluing or other methods known to those of ordinary skill in the art. In an embodiment, the top layer, absorbent layer and bottom layer are reversibly attached to the base layer by, for example, hook and loop fastener, zipper(s), adhesive, zipper, etc., such that the base layer can be removed from the three top layers and reused.

The absorbent bodily waste collection device of the present invention may be included in a kit, the kit comprising directions for use that explain, for example, how to insert the flexible frame member into the absorbent pad for use, how to remove the flexible frame member for reuse with another absorbent pad and how to dispose of soiled absorbent pads of the present invention. The absorbent bodily waste collection device kit of the present invention may also include product packaging and/or replacement absorbent pads for use with the reusable flexible frame member.

The absorbent bodily waste collection device of the present invention is not limited by size, shape or waste collection capacity. In an embodiment, various sizes are contemplated as various sized animals may require more or less absorbent (waste collection) capacity. Further, size may be determined by the specific use of the device. For example, the device may be sized for use in specific shapes or brands of animal carriers or animal crates. Shapes contemplated include, but are not limited to, square, rectangular, oval, round, etc. Further still, the absorbent layer of the absorbent waste collection device of the present invention may have varying amounts of absorbent material depending on the intended use.

The present invention further contemplates that the absorbent bodily waste collection device of the present invention may be sized to be used with humans. For example, one or more absorbent bodily waste collection devices of the present invention may be used in cribs, playpens or on beds.

The present invention contemplates an absorbent bodily waste collection device, comprising: a frame comprising one or more frame members, and an absorbent pad sized to hold the one or more flexible frame members, the absorbent pad comprising: a moisture permeable top layer, an absorbent middle layer, a moisture proof or substantially moisture proof bottom layer; and a base layer at least partially attached to one or more of said bottom, middle and top layers; wherein, when the one or more frame is positioned between the bottom layer and the base layer of the absorbent pad, the frame causes the absorbent pad to lay substantially flat.

The present invention further contemplates that the one or more frame members are flexible.

The present invention further contemplates that the frame essentially conforms to the shape of the adsorbent pad.

The present invention further contemplates that the frame is reversibly removable from between said base layer and said bottom layer.

The present invention further contemplates that the absorbent bodily waste collection device has a periphery and wherein the base layer is comprised of a first section with a peripheral edge and a distal edge, and a second section with a peripheral edge and a distal edge; said peripheral edge of the first section attached to at least a portion of the periphery of the absorbent bodily waste collection device and the peripheral edge of said second section attached to at least a portion of the periphery of said absorbent bodily waste collection device, the first section oriented at approximately 180 degrees from the second section of the base layer, wherein the distal edge of the first section of the base layer and the distal edge of the second section of the base layer touch, nearly touch or overlap.

The present invention further contemplates that the frame is comprised of a loop of spring metal or plastic.

The present invention further contemplates that the frame assumes an essentially circular configuration when not positioned in the absorbent pad.

The present invention further contemplates that the frame comprises one, two, three or four frame members.

The present invention further contemplates that the frame members may be circular, substantially straight or straight.

The present invention further contemplates that the surface area of the base layer is at least 20, 30, 40, 50, 60, 70, 80, 90 100, 110 or 120 percent of the surface area of the bottom layer. That is, in some embodiments that base layer may extend beyond the edge of the upper portion.

The present invention further contemplates that the absorbent bodily waste collection device of the present invention is essentially square or rectangular and wherein the base layer comprises four sections located at the corners of the absorbent bodily waste collection device.

The present invention further contemplates that the absorbent bodily waste collection device of the present invention is essentially square or rectangular and wherein the base layer comprises two sections located at two opposing edges of the absorbent bodily waste collection device.

The present invention further contemplates that the absorbent bodily waste collection device of the present invention is essentially square or rectangular and wherein the base layer comprises material at the edge of the absorbent bodily waste collection device.

The present invention contemplates a method of collecting urine waste, the method comprising: providing i) the absorbent bodily waste collection device of the present invention, and ii) an animal in need of urinating; directing the animal to the absorbent bodily waste collection device and maintaining the animal on the absorbent bodily waste collection device until the animal urinates. The animal may be maintained on the absorbent bodily waste collection device by any means known in the art including, but not limited to, holding, crating or training.

The present invention further contemplates a method of preventing the soiling of a bed or other article of furniture (e.g., chairs (including lounge chairs), sofas, ottomans and hassocks, divans, etc.) with urine waste, the method comprising placing an absorbent bodily waste collection device of the present invention on an article of furniture to be protected from urine waste prior to the use of that article of furniture by a human or other animal that may have difficulty controlling urination. The absorbent bodily waste collection device of the present invention may be sized to cover all surfaces usable by the human or other animal or may be sized to cover only the area or areas that are most likely to become soiled if the human or other animal does not maintain bladder control or otherwise loses bladder control.

The description, and referenced figures, of the present invention show certain embodiments of the present invention but are not to be considered limiting of the scope of the invention as other features and advantages of the invention will be apparent to one of skill in the art from the following description and figures.

BRIEF DESCRIPTION OF DRAWINGS

FIG. 2A shows a flexible frame element of the present invention. FIG. 2B shows a view of the flexible frame element inserted into the absorbent pad of the present invention. The view is from the back of the pad with the opening for the flexible frame element in the base layer shown. The flexible frame element, although visible in the figure, is located inside the absorbent pad and viewed in the figures as though the base layer were transparent or translucent.

FIGS. 8 A & B show additional embodiments of the opening on the base layer of the absorbent pad element of the present invention. (A) shows an opening comprising two flaps that nearly or slightly overlap, the opening being where the two flaps approach each other. (B) shows the base layer extending from the edge of the absorbent pad, wherein the frame element of the present invention is inserted.

DETAILED DESCRIPTION OF PREFERRED EMBODIMENTS

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow. An patterns shown are for ornamentation only and are not considered part of the invention unless stated otherwise.

While the invention has been described with respect to a limited number of embodiments, those skilled in the art, having benefit of this disclosure, will appreciate that other embodiments can be devised which do not depart from the scope of the invention as disclosed herein.

Figure 1A:
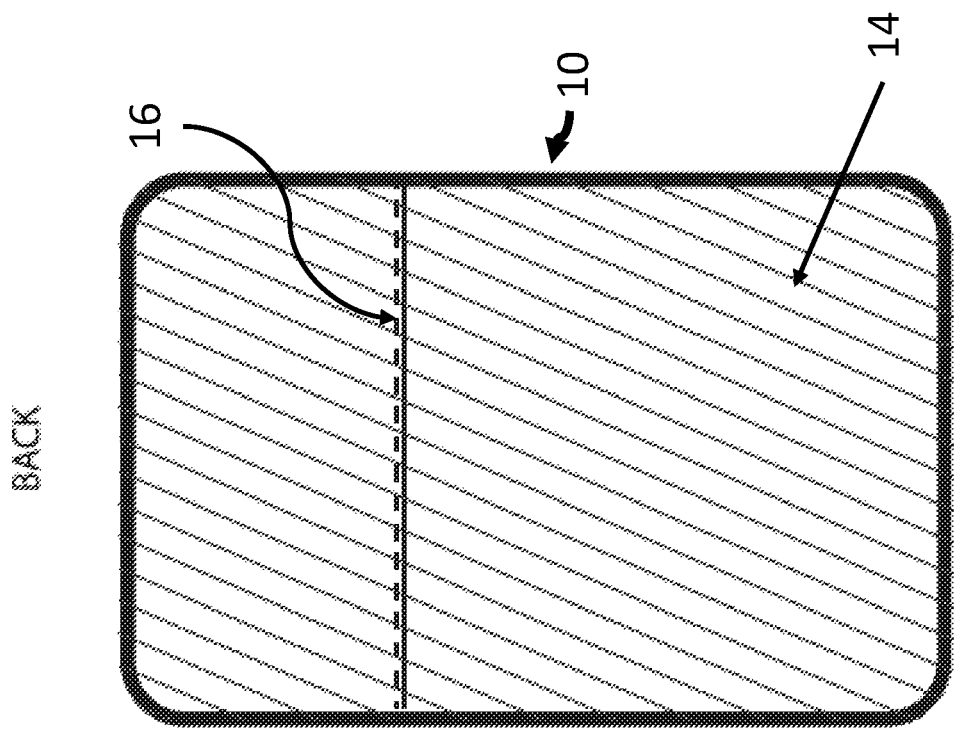
FIGS. 1 A & B show a front (A) and back (B) view of a representative absorbent bodily waste collection device of the present invention.
FIG. 1C shows a cross-sectional stylized representation of the absorbent bodily waste collection device of the invention (not to scale) at the position indicated in FIG. 1A.
Figure 1B:
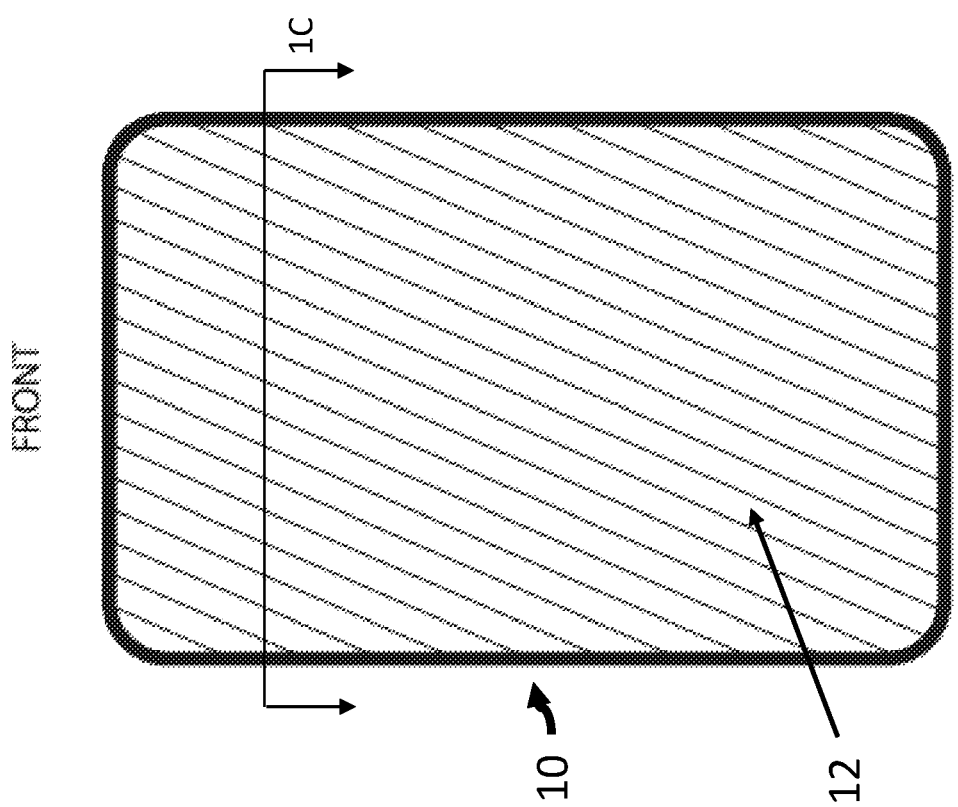

FIG. 1A shows a top view of an embodiment of the absorbent bodily waste collection device 10 of the present invention. The moisture permeable top layer 12 is shown. FIG. 1B shows a bottom view of an embodiment of the absorbent bodily waste collection device 10 of the present invention. The base layer 14 and the opening 16 to permit the insertion/removal of the frame of the present invention are shown.

Figure 1C:
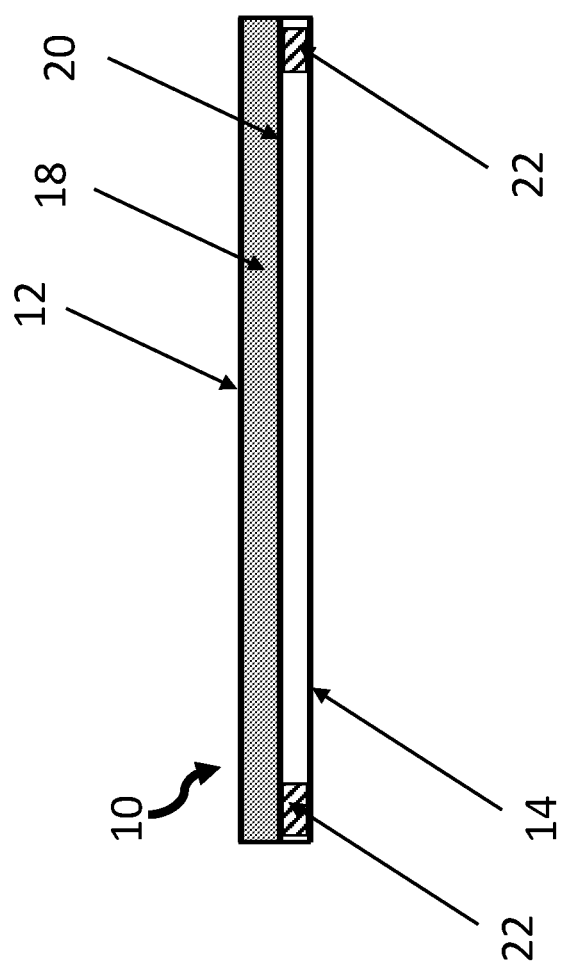

FIG. 1C shows a stylized cross-sectional view of the absorbent bodily waste collection device 10 of the present invention at the position indicated in FIG. 1A. Shown are the moisture permeable top layer 12, the absorbent middle layer 18, a moisture proof or substantially moisture proof bottom layer 20, the base layer 14 and the frame 22. The figure is not to scale. The moisture permeable top layer, absorbent layer, moisture proof or substantially moisture proof layer and base layer collectively are referred to as the absorbent pad (see, FIG. 3, element 30). When the frame is inserted into the absorbent pad between the bottom layer and the base layer, the absorbent pad and frame comprise the absorbent bodily waste collection device 10 of the present invention.

FIG. 2A shows a frame 22 suitable for use in the present invention. The frame is made, for example, from a flexible material such as spring metal or plastic. FIG. 2B shows the frame 22 inserted into and in place in the absorbent pad of the present invention. For purposes of clarity with regard to showing the placement of the frame within the absorbent pad, the base layer is represented as transparent or translucent in the figure. The opening in the base layer 16 is shown.

Figure 3:
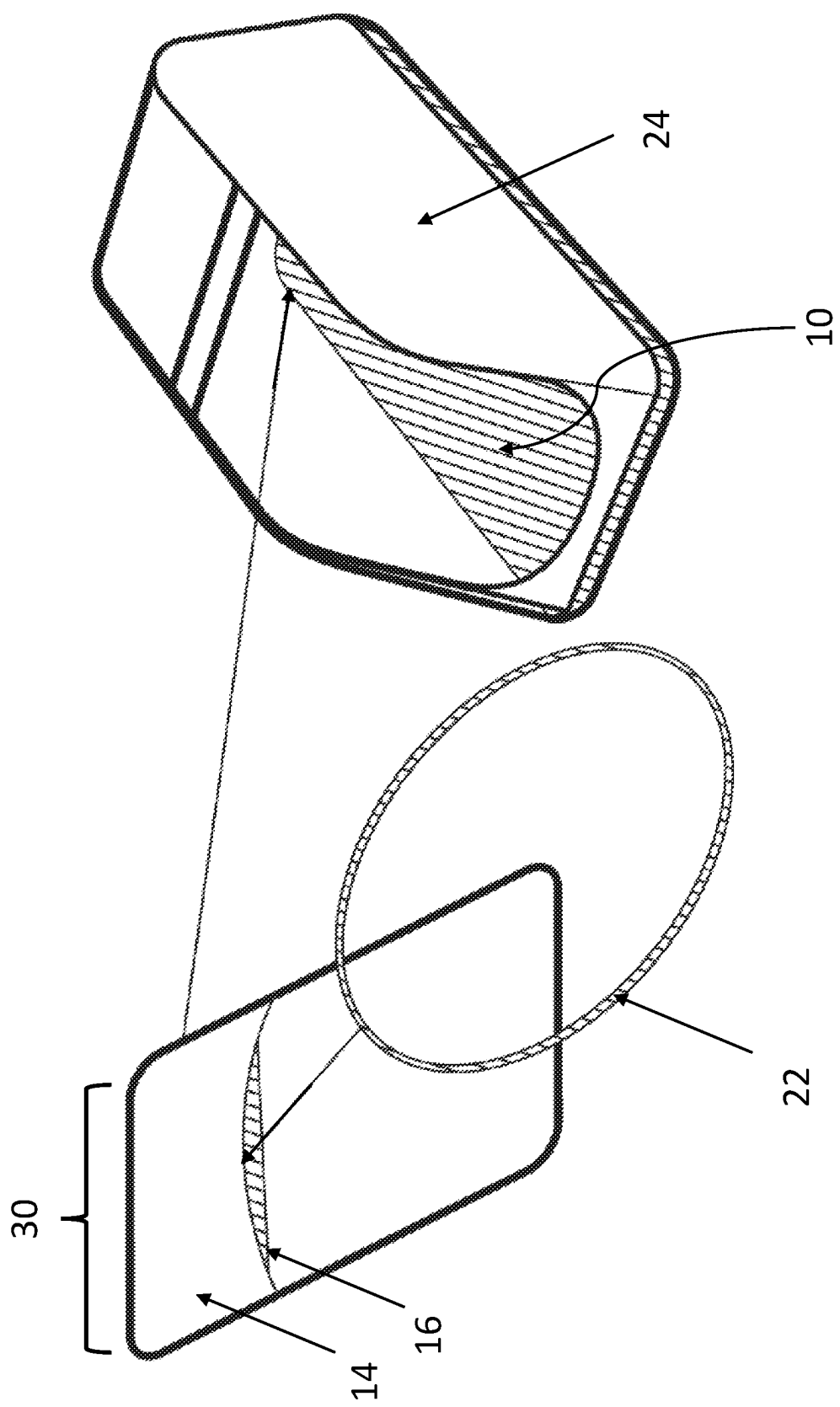
FIG. 3 shows the insertion of a flexible frame element into an absorbent pad of the present invention and the insertion of the absorbent pad into a pet carrier.

FIG. 3 shows the insertion of the frame 22 into the absorbent pad 30 via opening 16 in the base layer 14 and the placement of the absorbent bodily waste collection device 10 of the present invention into a pet carrier 24 for use.

Figure 4:
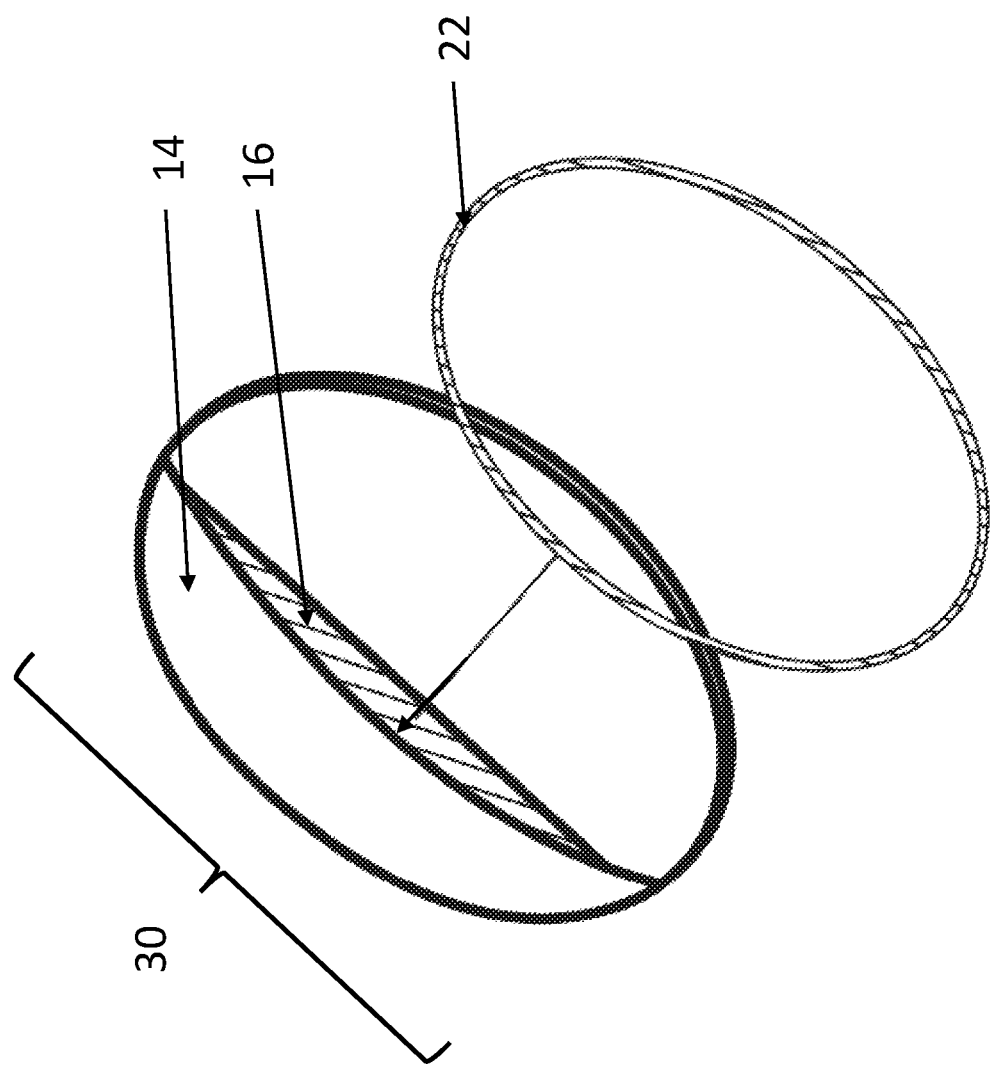
FIG. 4 shows the insertion of a flexible frame element of the present invention into a round absorbent pad of the present invention.

FIG. 4 shows a round-shaped absorbent pad 30 with frame 22 being inserted via opening 16 in the base layer 14.

Figure 5:
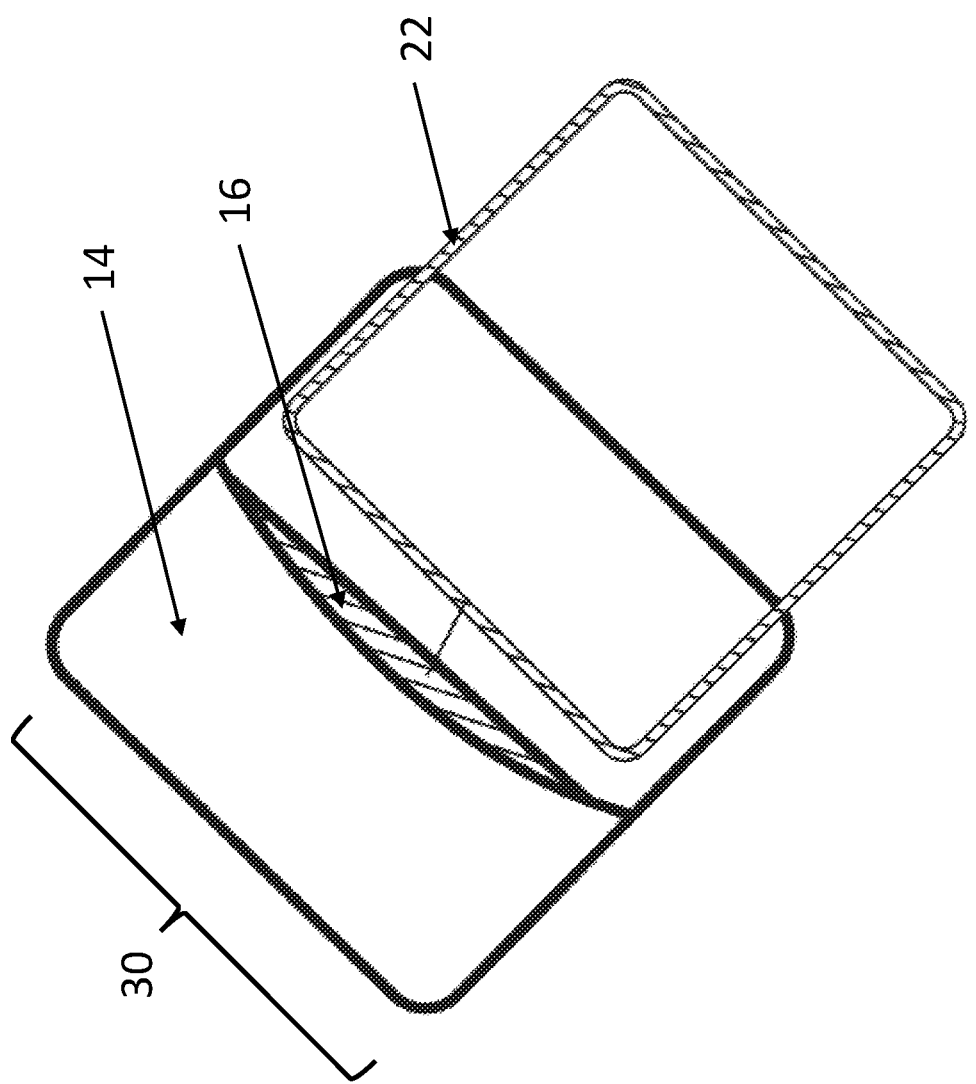
FIG. 5 similarly shows the insertion of a flexible frame element of the present invention into a square-shaped absorbent pad of the present invention.

FIG. 5 shows square-shaped absorbent pad 30 with a square-shaped frame 22 being inserted via opening 16 in the base layer 14.

Figure 6B:
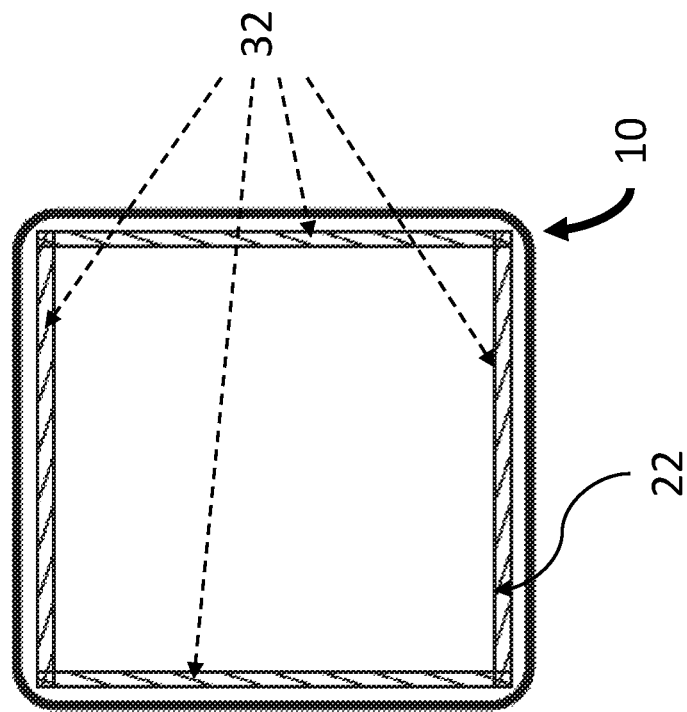
FIGS. 6 A & B show different embodiments of the frame element of the present invention. (A) shows a rounded frame element assuming a square shape after insertion into an absorbent pad of the present invention. (B) shows a frame element of the present invention comprising four straight elements joined at the ends to form a square. Although the flexible frame members are visible in the figures, they would be positioned inside the absorbent pad between the bottom layer and base layer.
Figure 6A:
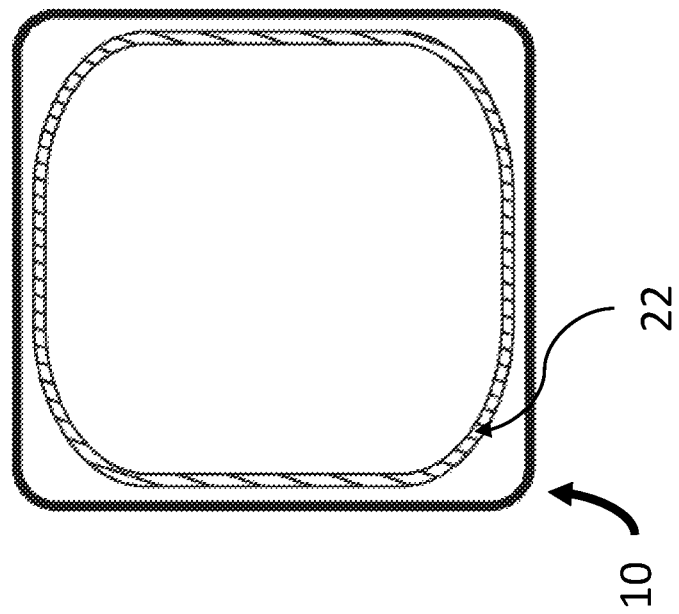

FIG. 6 shows two different square-shaped frames 22 in an absorbent bodily waste collection device 10 of the present invention. (A) shows a square-shaped frame 22 with rounded corners. (B) shows a square-shaped frame 22 comprising four frame members 32 (dashed lines) connected at the ends to form a square. For purposes of clarity with regard to showing the placement of the frame within the absorbent pad, the base layer is represented as transparent or translucent in the figure.

FIG. 7 shows two different square-shaped absorbent bodily waste collection devices 10 of the present invention. (A) shows a frame made from three frame members 32 (dashed lines) and arranged to form an H-shape. (B) shows a frame made from two frame members 32 (dashed lines) and arrange to form an X-shape. For purposes of clarity with regard to showing the placement of the frame within the absorbent pad, the base layer is represented as transparent or translucent in the figure.

FIG. 8 shows a bottom view of two different absorbent bodily waste collection device 10 of the present invention. (A) shows an absorbent bodily waste collection device 10 of the present invention with the base layer 14 comprising two sections that touch, nearly touch or overlap slightly to form an opening 16. (B) shows a base layer 14 at the periphery of the absorbent bodily waste collection device leaving the moisture proof or substantially moisture proof bottom layer 20 substantially visible. A frame is positioned under the base layer 14 (not visible).

Figures 7A, 7B:
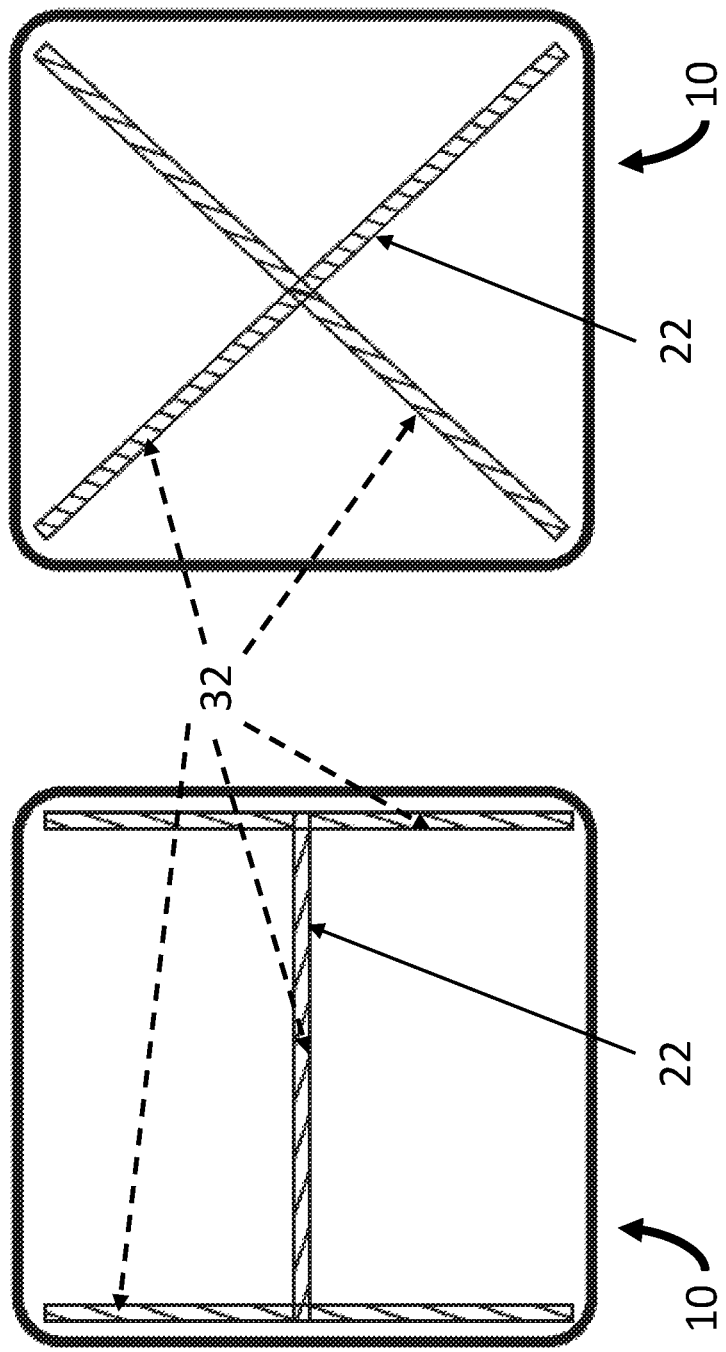
FIGS. 7 A & B show more additional embodiments of the frame element of the present invention. (A) shows a frame element comprising three straight elements positioned to form an "H" pattern. (B) shows a frame element comprising two straight elements positioned to form an "X" pattern. Although the flexible frame members are visible in the figures, they would be positioned inside the absorbent pad between the bottom layer and base layer.
Figure 9B:
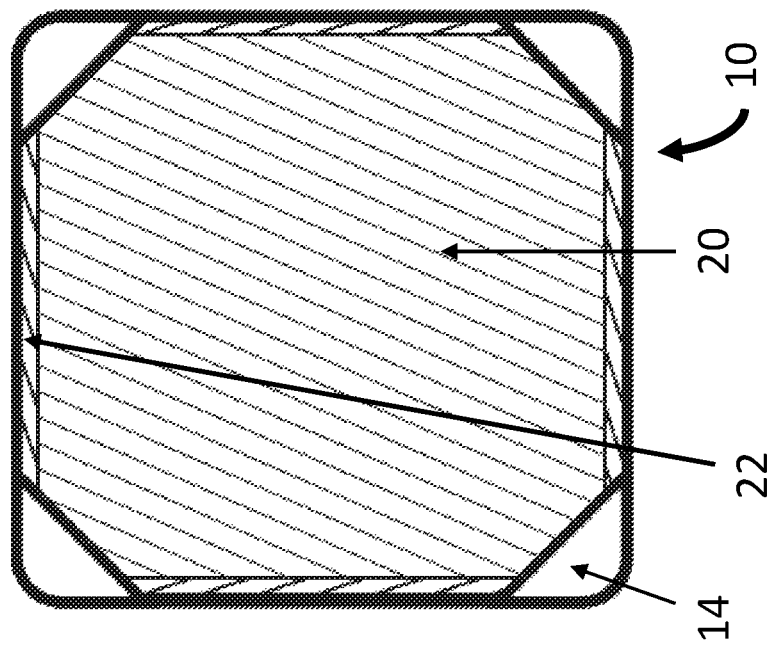
FIGS. 9 A & B show additional embodiments of the opening on the base layer of the absorbent pad of the present invention. (A) shows the base layer extending from the edge of the base layer similarly to FIG. 8B but extending further under the absorbent pad. (B) shows the base layer forming essentially triangular shaped corners on the absorbent pad suitable for retaining an "X"-shaped or a square-shaped frame element of the present invention.
Figure 9A:
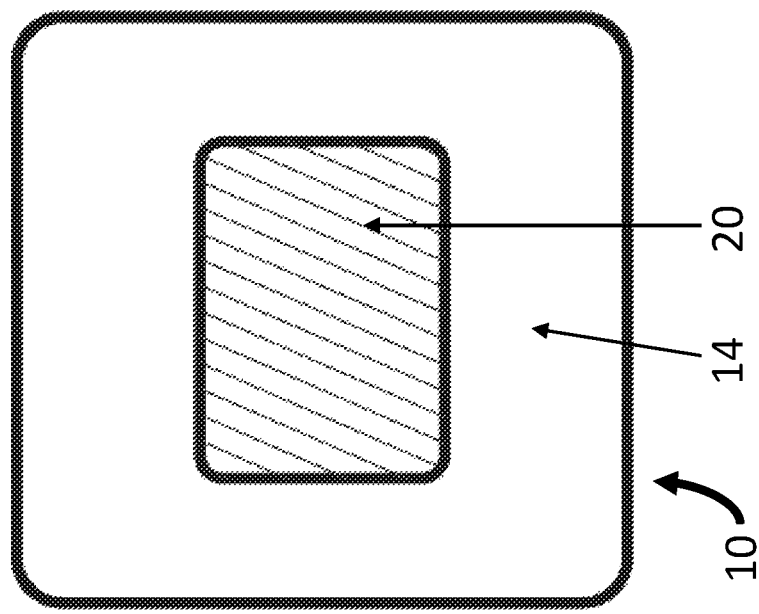

FIG. 9 shows a bottom view of two additional absorbent bodily waste collection device 10 of the present invention. (A) shows an absorbent bodily waste collection device 10 of the present invention with the base layer 14 extending from the periphery of the absorbent bodily waste collection device leaving the moisture proof or substantially moisture proof bottom layer 20 partially visible. A square-shaped frame is positioned under the base layer 14 (not visible). (B) shows an absorbent bodily waste collection device 10 of the present invention with the base layer 14 forming triangular shapes at the corners of the absorbent bodily waste collection device leaving the moisture proof or substantially moisture proof bottom layer 20 substantially visible. A square-shaped frame 22 is positioned such that the corners of the frame are positioned under the base layer triangular portions 14. In other embodiments, the frame may be comprised of two or three frame members, as shown in FIGS. 7B and 7A, respectively.

What is claimed is:

1. An absorbent bodily waste collection device, comprising:
   a. a frame comprising one or more frame members, and
   b. an absorbent pad sized to hold the one or more frame members, the absorbent pad comprising:
      i. a moisture permeable top layer,
      ii. an absorbent middle layer,
      iii. a moisture proof or substantially moisture proof bottom layer; and
      iv. a base layer at least partially attached to one or more of said bottom, middle, and top layers;
   c. wherein, when the one or more frame members are positioned between the bottom layer and the base layer of the absorbent pad, the frame causing the absorbent pad to lay substantially flat, and
   d. the frame is reversibly removable from between said base layer and said bottom layer.

2. The absorbent bodily waste collection device of claim 1, wherein said one or more frame members are flexible.

3. The absorbent bodily waste collection device of claim 1, wherein said frame essentially conforms to the shape of the adsorbent pad.

4. The absorbent bodily waste collection device of claim 1, wherein said absorbent bodily waste collection device has a periphery and wherein said base layer is comprised of a first section with a peripheral edge and a distal edge, and a second section with a peripheral edge and a distal edge; said peripheral edge of said first section attached to at least a portion of said periphery of said absorbent bodily waste collection device and said peripheral edge of said second section attached to at least a portion of said periphery of said absorbent bodily waste collection device, the first section oriented at approximately 180 degrees from the second section of the base layer, wherein the distal edge of the first section of the base layer and the distal edge of the second section of the base layer touch, nearly touch or overlap.

5. The absorbent bodily waste collection device of claim 1, said frame is comprised of a loop of either spring metal or plastic.

6. The absorbent bodily waste collection device of claim 5, wherein the frame assumes an essentially circular configuration when not positioned in the absorbent pad.

7. The absorbent bodily waste collection device of claim 1, wherein said frame comprises one, two, three or four frame members.

8. The absorbent body waste collection device of claim 7, wherein said frame members are substantially straight or straight.

9. The absorbent bodily waste collection device of claim 1, wherein the surface area of said base layer is at least 20 percent of the surface area of the bottom layer.

10. The absorbent bodily waste collection device of claim 1, wherein the absorbent bodily waste collection device is essentially square or rectangular and wherein the base layer comprises four sections located at the corners of the absorbent bodily waste collection device.

11. The absorbent bodily waste collection device of claim 1, wherein the absorbent bodily waste collection device is essentially square or rectangular and wherein the base layer comprises two sections located at two opposing edges of the absorbent bodily waste collection device.

12. The absorbent bodily waste collection device of claim 1, wherein the absorbent bodily waste collection device is essentially square or rectangular and wherein the base layer comprises material at the edge of the absorbent body waste collection device.

13. A method of collecting urine waste, comprising:
a. providing i) the absorbent bodily waste collection device of claim 1, and ii) an animal in need of urinating;
b. directing the animal to the absorbent bodily waste collection device and maintaining the animal on the absorbent bodily waste collection device until the animal urinates.

* * * * *